United States Patent [19]

Farnsworth

[11] Patent Number: 5,137,765

[45] Date of Patent: Aug. 11, 1992

[54] DERIVATIZED GLASS SUPPORTS FOR PEPTIDE AND PROTEIN SEQUENCING

[75] Inventor: Vincent Farnsworth, Agoura, Calif.

[73] Assignee: Porton Instruments, Inc., Tarzana, Calif.

[21] Appl. No.: 581,936

[22] Filed: Sep. 13, 1990

Related U.S. Application Data

[62] Division of Ser. No. 228,524, Aug. 5, 1988, Pat. No. 4,992,383.

[51] Int. Cl.$^5$ ............... B32B 17/06; B32B 33/00; C12Q 1/68; G01N 1/18; G01N 33/68
[52] U.S. Cl. ............................... 428/64; 428/288; 428/289; 428/429; 435/6; 436/89; 436/178
[58] Field of Search ............ 428/429, 64, 288, 289; 435/6; 436/89, 178

[56] References Cited

U.S. PATENT DOCUMENTS

| | | |
|---|---|---|
| 3,519,538 | 7/1970 | Messing . |
| 3,652,761 | 3/1972 | Weetal . |
| 4,034,139 | 7/1977 | Mazargull et al. . |
| 4,233,366 | 11/1980 | Sample et al. . |
| 4,338,377 | 7/1982 | Beck et al. ............... 428/428 |
| 4,447,495 | 5/1984 | Engle ........................ 428/429 |
| 4,490,436 | 12/1984 | Kawalsami et al. ........ 428/403 |
| 4,548,904 | 10/1985 | Kent et al. ................. 436/89 |
| 4,603,114 | 7/1986 | Hood et al. ................ 436/89 |
| 4,705,725 | 11/1987 | Glajch et al. .............. 428/405 |
| 4,748,121 | 5/1988 | Beaver et al. .............. 435/176 |
| 4,833,093 | 5/1989 | Malmquist et al. ........ 436/527 |
| 5,001,011 | 3/1991 | Plueddemann ............ 428/429 |
| 5,032,455 | 7/1991 | Dana et al. ................ 428/429 |

OTHER PUBLICATIONS

Meuth et al., "Stepwise Sequence Determinination from the Carboxy Terminus of Peptides" *Biochemistry*, 1982, vol. 21, pp. 3750–3757.

Laursen et al., "Solid Phase Methods in Protein Sequence Analysis Methods of Biochemical Analysis", vol. 26 John Wiley & Sons, Inc. 1980, pp. 202–215.

*Primary Examiner*—James C. Cannon
*Attorney, Agent, or Firm*—Iver P. Cooper

[57] ABSTRACT

Peptides or proteins are sequenced by stepwise degradation while immobilized on a glass support derivatized with a silica-binding substance bearing a free acid group, especially a sulfonic acid group. The support is preferably derivatized with 2-(4-chlorosulfonyl phenyl) ethyl trimethoxysilane.

Peptide sequencing performance is improved if the support is also derivatized with a monomeric silica-binding substance bearing a free quaternary ammonium group, such as N-trimethyoxysilyl propyl -N,N,N-trimethyl ammonium chloride.

9 Claims, 20 Drawing Sheets

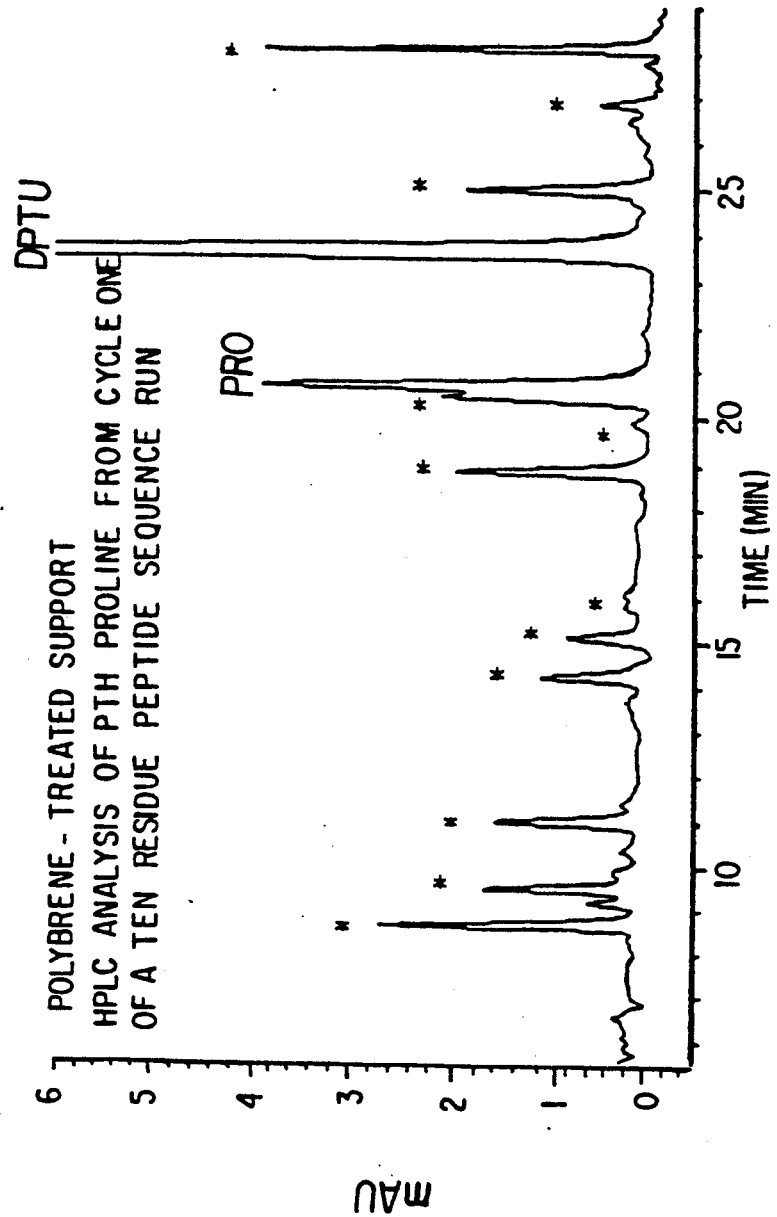

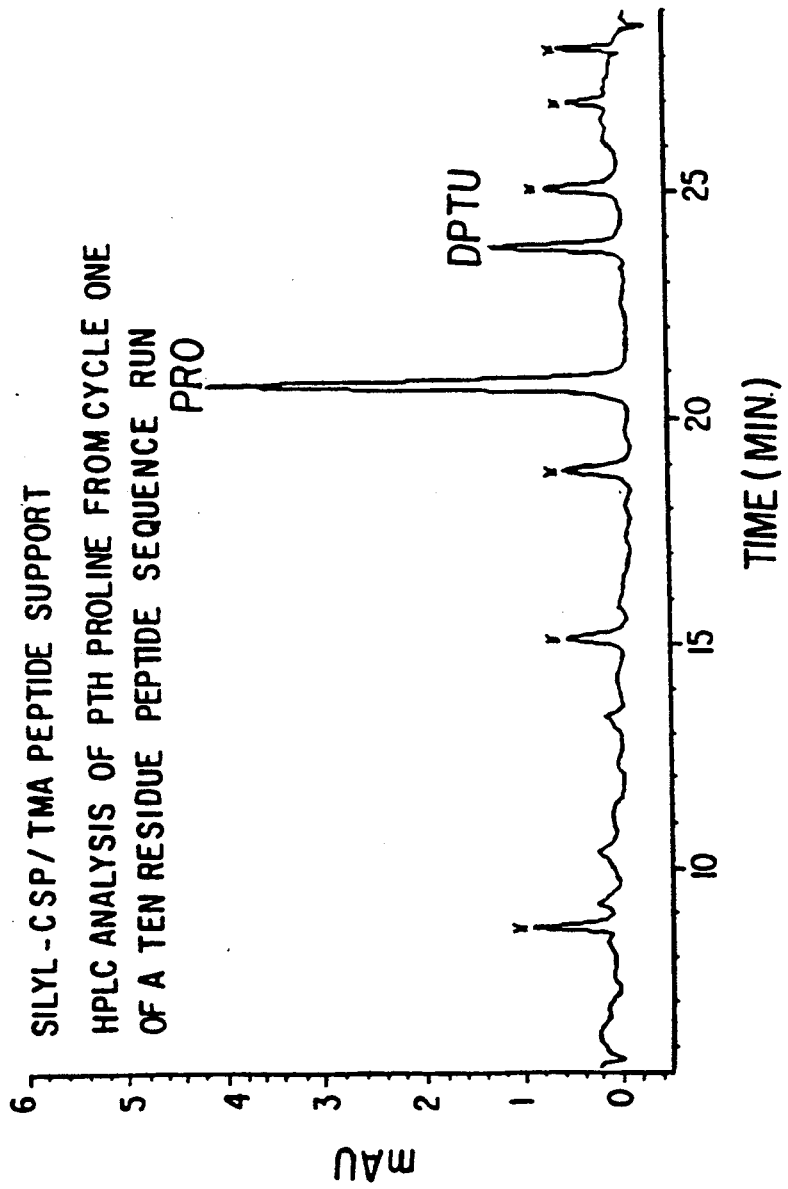

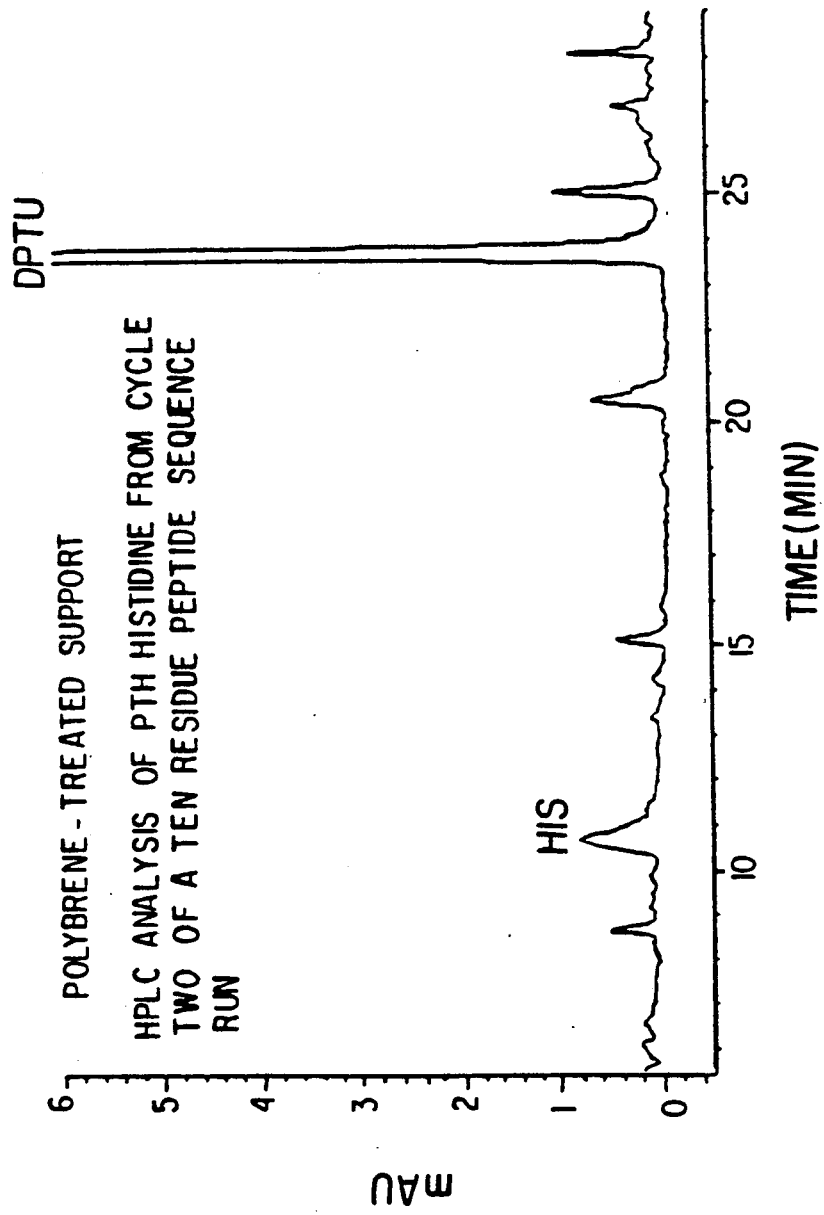

SILYL-CSP/TMA PEPTIDE SUPPORT
HPLC ANALYSIS OF PTH HISTIDINE FROM CYCLE TWO OF A
TEN RESIDUE PEPTIDE SEQUENCE RUN

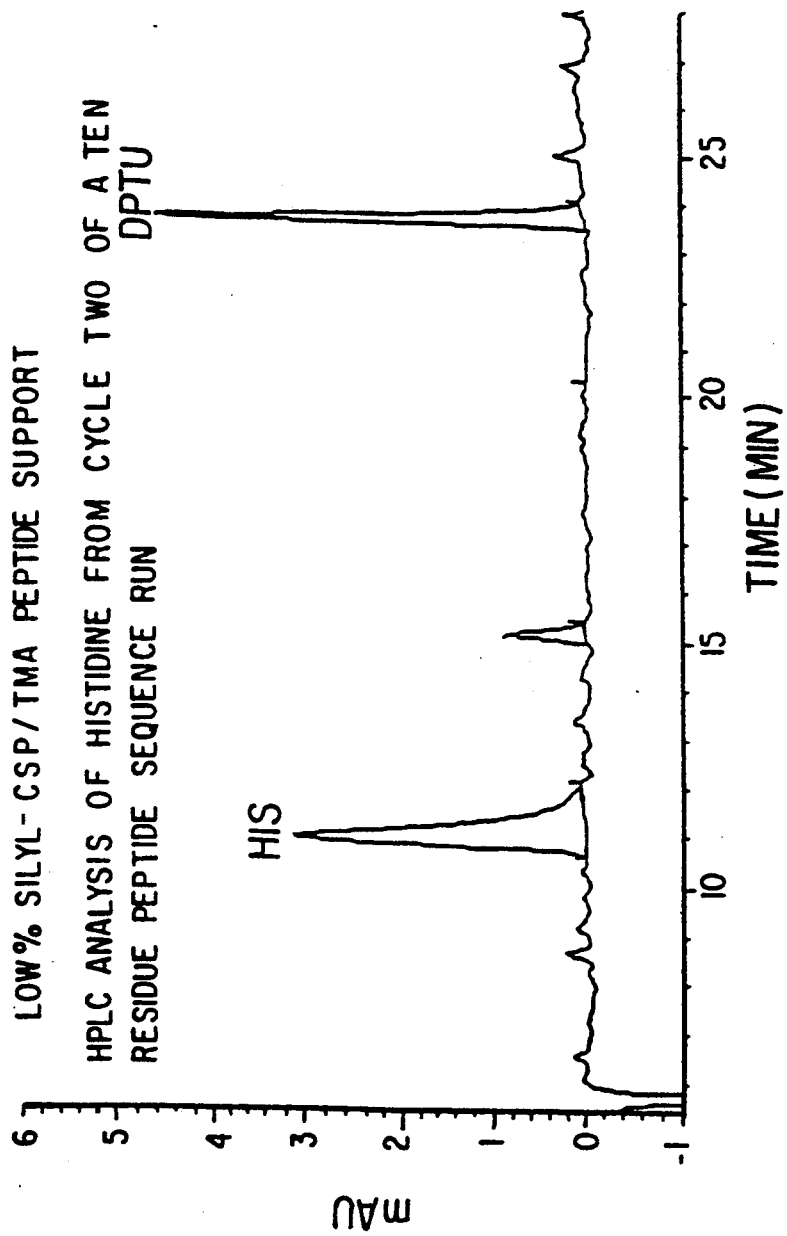

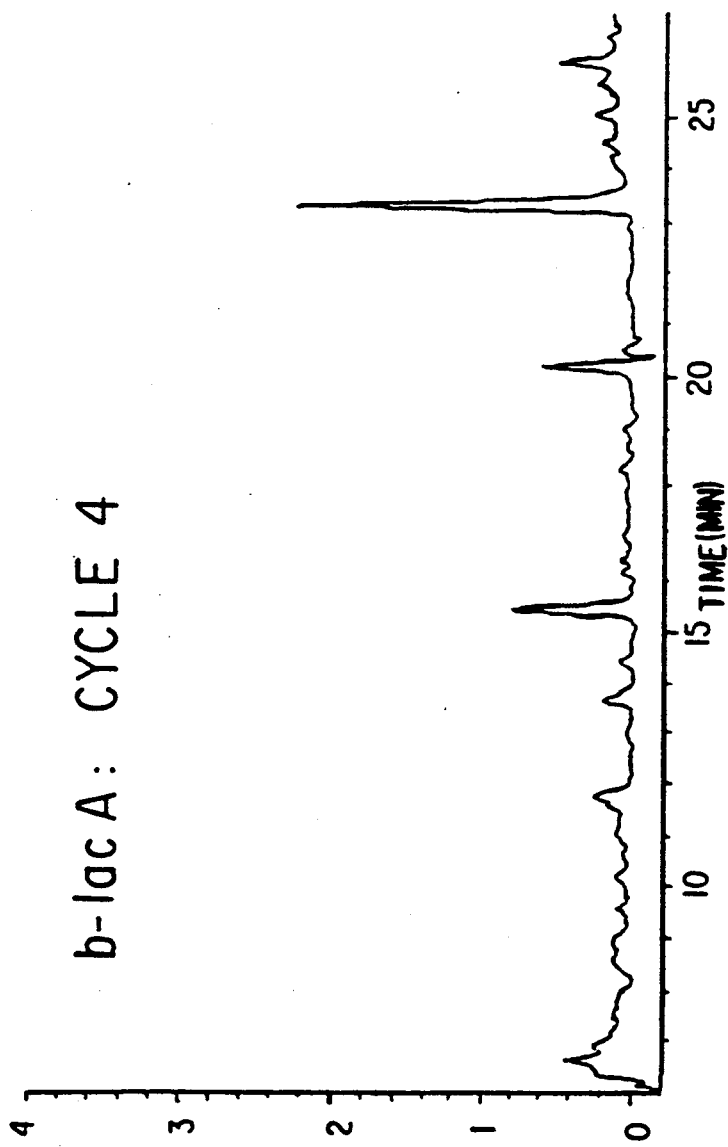

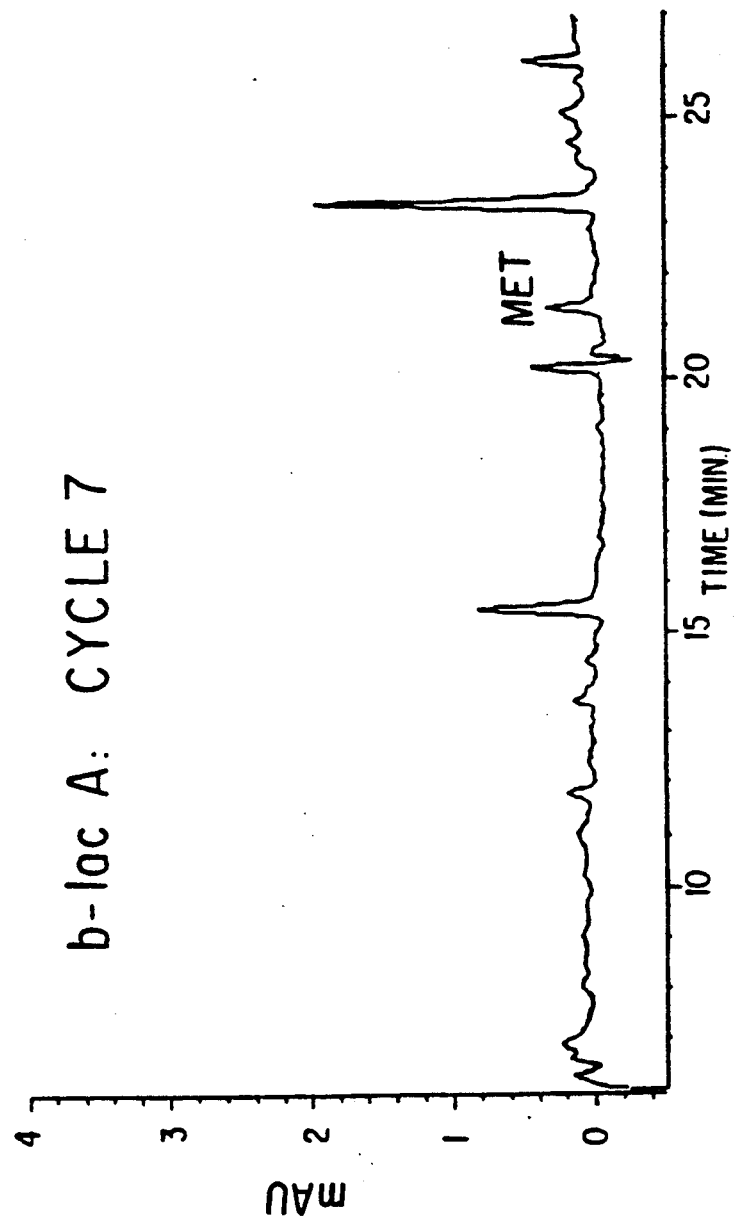

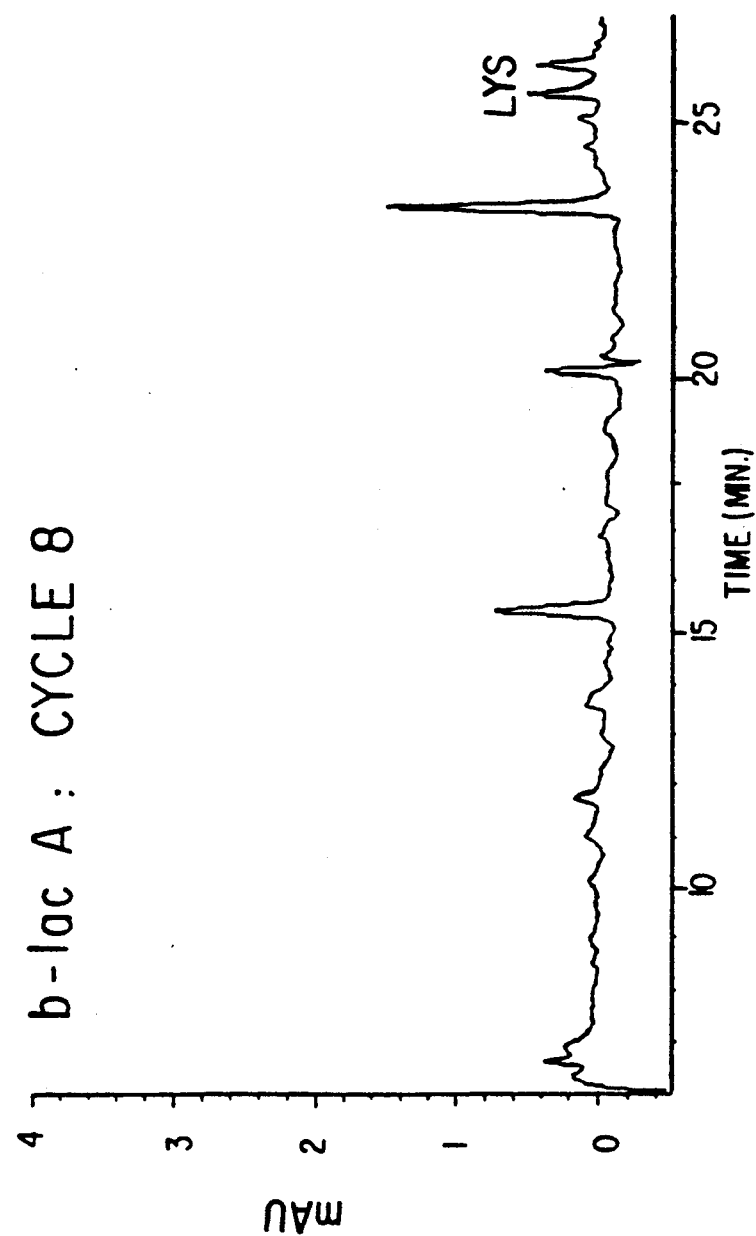

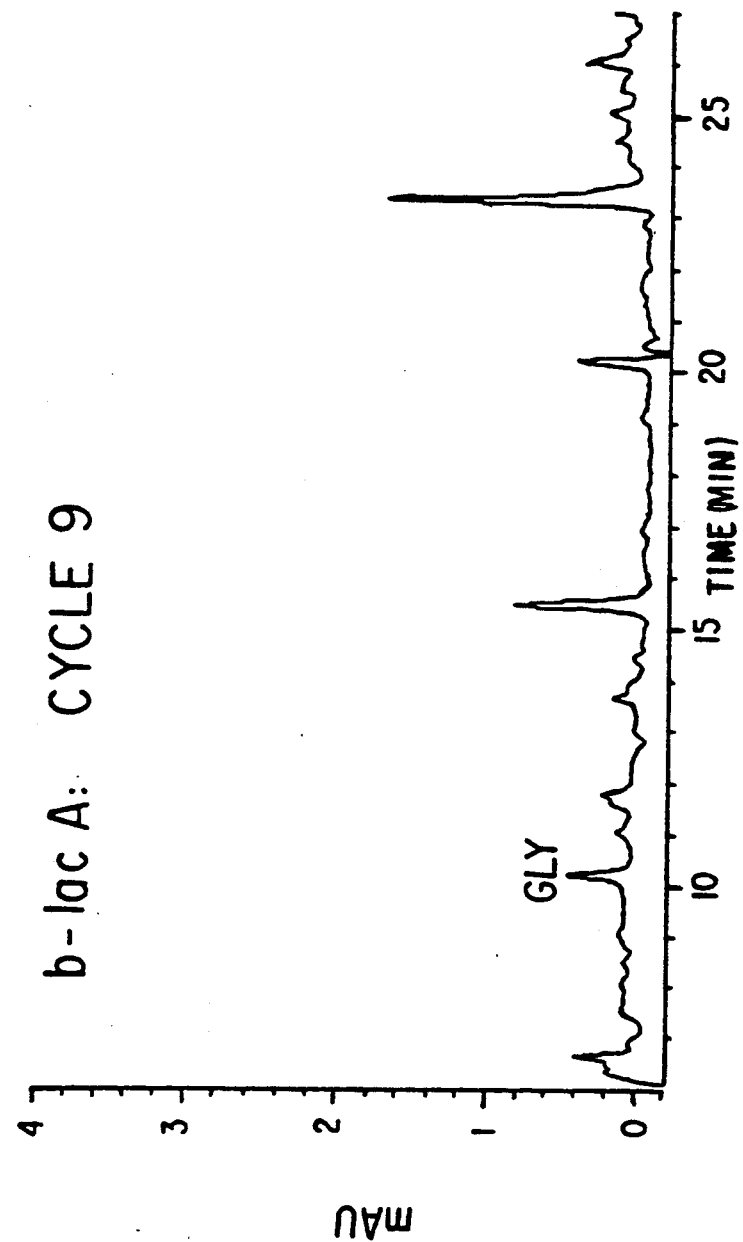

b-lac A: CYCLE 10 b-lac:A CYCLE 11

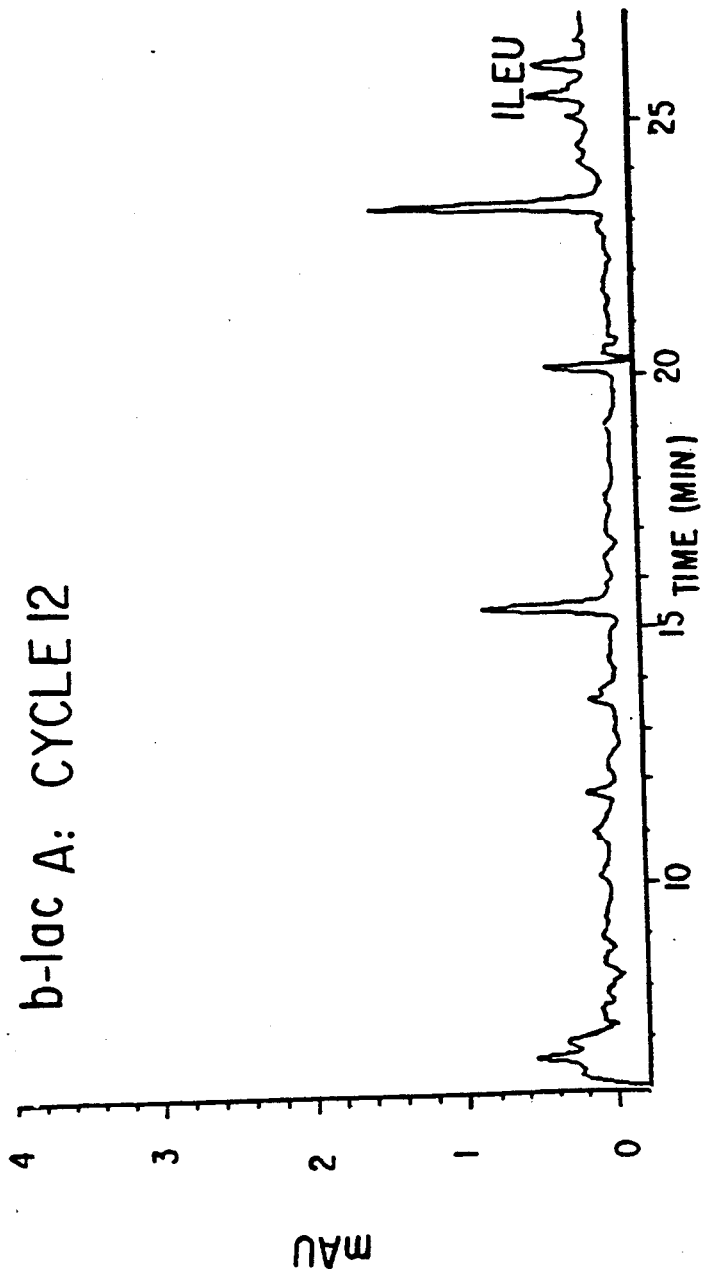

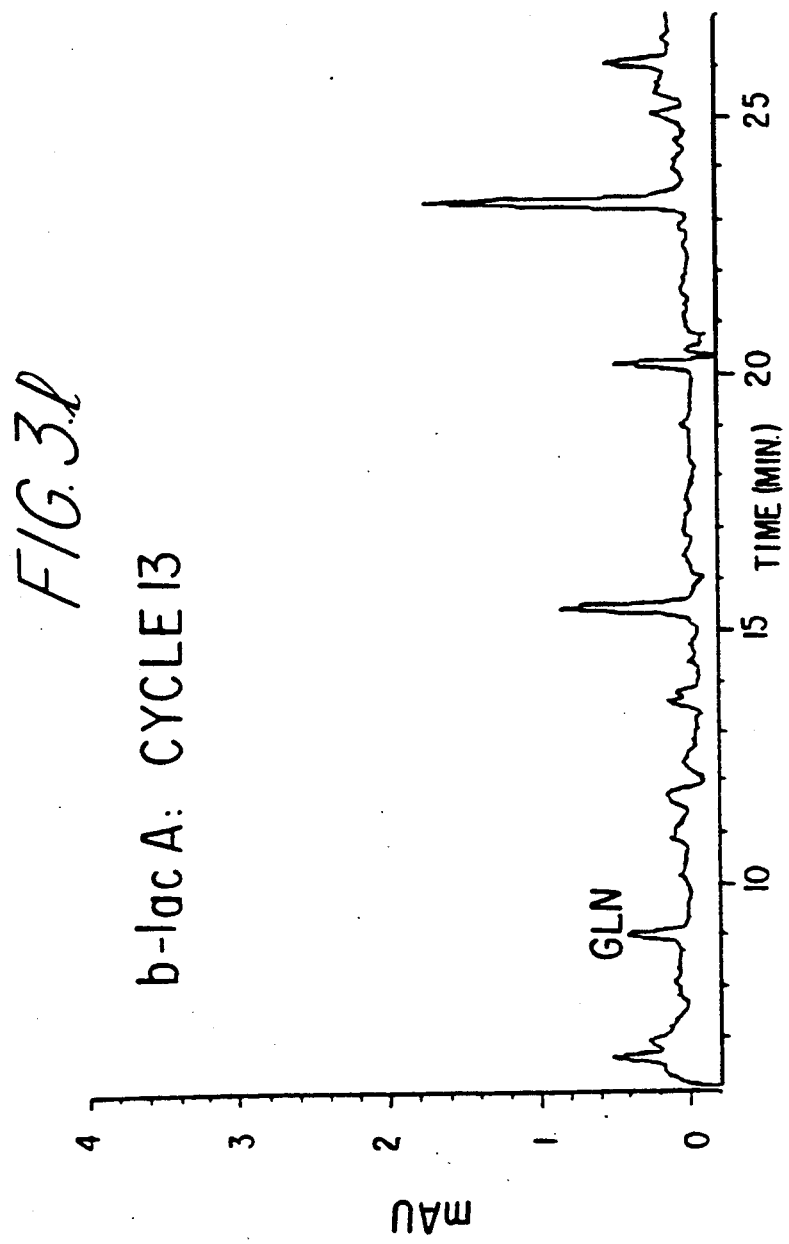
FIG. 3ℓ  b-lac A: CYCLE 13

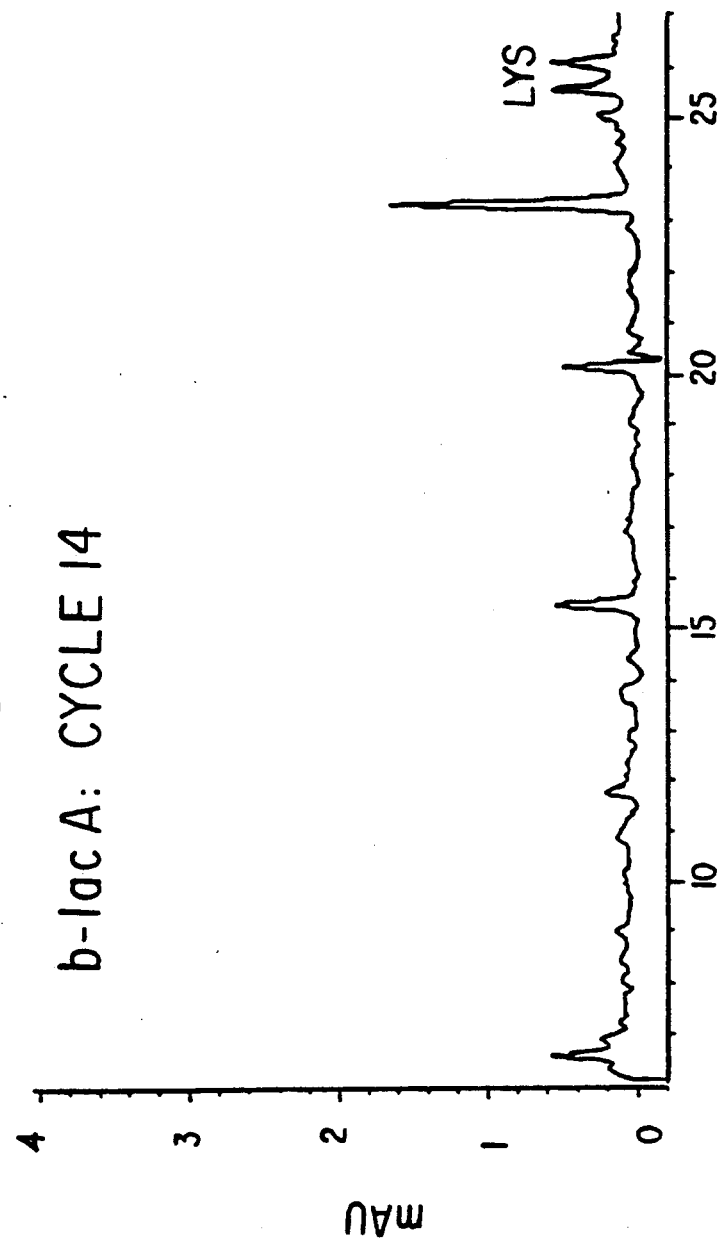

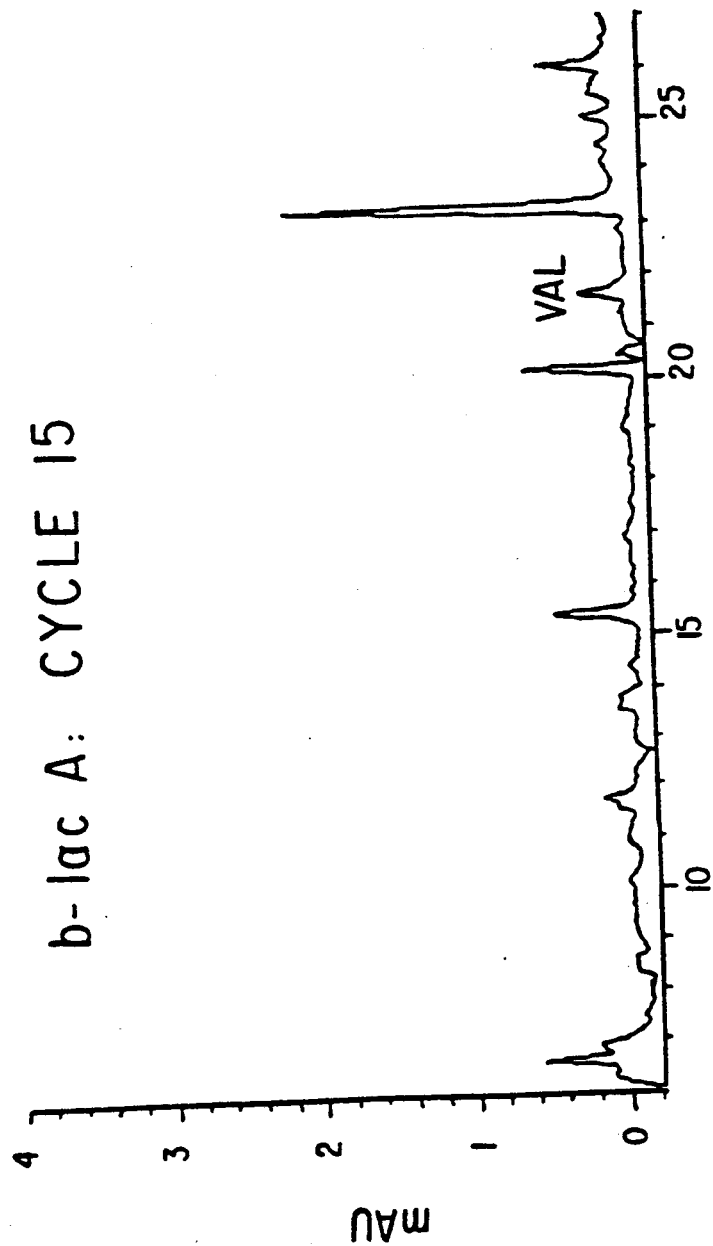

DERIVATIZED GLASS SUPPORTS FOR PEPTIDE AND PROTEIN SEQUENCING

This is a division of application Ser. No. 07/228,524 filed Aug. 5, 1988 now U.S. Pat. No. 4,992,383 hereby incorporated by reference herein.

BACKGROUND OF THE INVENTION

This invention relates to the use of a glass support derivatized with 2-(4-chlorosulfonylphenyl) ethyl trimethoxy silane (silyl CSP), N-trimethoxysilylpropyl-N,N,N-trimethyl ammonium chloride (silyl TMA) or a combination thereof, in the sequencing of peptides or proteins.

The primary sequence of amino acids in a peptide or protein is commonly determined by a stepwise chemical degradation process in which amino acids are removed one-by-one from one end of the peptide, and identified. In the Edman degradation, the N-terminal amino acid of the peptide is coupled to phenylisothiocyanate The ATZ amino acid, which is highly unstable, is extracted and converted into the more stable phenylthiohydantoin (PTH) derivative and identified by chromatography. The residual peptide is then subjected to further stepwise degradation.

Automatic protein sequencers in which the Edman degradation reactions are carried out in a film on the inside surface of spinning cup are known. Edman and Begg, Eur. J. Biochem., 1:80 (1967); Penhast, U.S. Pat. No. 3,725,010. A quaternary ammonium salt, 1,5-dimethyl-1,5-diazundecamethylene polymethobromide (Polybrene) has been used as a sample carrier.

Schroeder, Meth. Enzymol., 11:445 (1967) and Jentsch, Jr., Proc. First Int'l Conf. on Meth. in Protein Sequence Anal. 193 (1975) modified the liquid phase Edman degradation by first non-chemically depositing the protein or peptide onto a paper strip.

Laursen, Meth. Enzymnol., 25:344 (1972) covalently attached peptides to an insoluble resin prior to sequencing. Wachter, et al., FEBS Lett., 35: 97 (1973) immobilized the peptides on controlled pore glass beads derivatized with 3-aminopropyltriethoxysilane. The resulting aminopropyl glass binds to free carboxyl groups of the peptides. Dreyer, U.S. Pat. No. 4,065,412 favors immobilizing the peptides, either by covalent linkage or by adsorption, onto a macroporous reaction support surface of polystyrene or glass.

Hood, U.S. Pat. Nos. 4,704,256 and 4,603,114 teaches embedding the sample in a permeable solid matrix formed as a thin film on a support such as a glass fiber sheet. The matrix is preferably a polymeric quaternary ammonium salt, since the positively charged quaternary ammonium groups interact strongly with the negatively charged glass surface.

FIGS. 17A, 17B and 17C in the Hood patents illustrate three approaches to improving sample retention by immobilizing the protein or peptide. FIG. 17A shows covalent attachment to derivatized glass, as in Wachter. FIG. 17B shows physical adsorption of the sample to the support, as in Schroeder. FIG. 17C illustrates embedding the sample in a matrix covering the glass, as in Hood.

Saunders, U.S. Pat. No. 3,987,058 discloses the use of sulfonated aralkyl silicas as cation exchangers. The sodium salt of sulfobenzylsilica was used to separate nitrosoproline from proline and other components of cured meat samples. There is no discussion of protein sequencing.

Glajch, U.S. Pat. No. 4,705,725 relates particularly to support structures comprising silica to which is covalently attached a monofunctional saline containing at least two sterically protecting groups attached to the silicon atom of the silane. For use in peptide sequencing, this silane is substituted with a quaternary amino group so as to interact with peptides in a manner similar to that of Polybrene. For use in cation exchange chromatography, this silane is substituted with a $-(CH_2)_3-C_6H_4-SO_3H$ group.

Silanes have been used to couple antigens or antibodies to glass. Weetall, U.S. Pat. No. 3,652,761.

SUMMARY OF THE INVENTION

Present methods of gas-phase or so-called pulsed-liquid protein sequencing rely on embedding the sample in a matrix (Hood) or covalent attachment of the sample to a support (Laursen). This is to prevent dislodging the sample from the support during liquid solvent washes and transfers. Covalent attachment has the advantage of permanently locating the sample in the reaction chamber without danger of dislodging it during liquid-phase chemistry or washing. The disadvantages are extra chemical reactions to attach the sample to the reaction support, inefficiencies inherent in these attachment procedures and low yields of residues in the sample which are involved in the attachment to the support. Sample embedding has the advantage of being a more or less universal immobilization method without the extra sample manipulation associated with covalent attachment. Major disadvantages include high levels of contaminating artifacts on analytical systems used for PTH amino acid identification and the necessity to run the sequencer for several cycles before the actual sample is loaded. Also, it is common practice to add amines which act as scavengers of these amino-reactive contaminants which would otherwise react with the N-terminal amino group of the sample and block it to Edman degradation. Since many of these contaminants show up as artifacts in PTH analysis (see FIGS. 1A and 1B), the sequencer must be run for several cycles to lower the level of these artifacts before the sample is loaded. This "precycling," as it has come to be known, uses expensive chemicals and valuable time. Another disadvantage of carrier methods relates to the Edman chemicals and washing solvents having to diffuse into and out of the matrix. Since the sample is trapped within a matrix and not fully exposed on the surface of the support, reaction and washing efficiency may be compromised.

We have found that certain derivatized glass supports bind peptides and proteins well enough to minimize loss of the sample during solvent and reagent delivery, while still releasing the amino acid derivatives as they are cleaved during the degradation process. These are "silyl CSP," 2-(4-chlorosulfonyl phenyl) ethyl trimethoxysilane, and "silyl TMA," N-trimethoxysilyl propyl -N,N,N-trimethyl ammonium chloride.

Both the protein and peptide supports are made by chemical modification of the surface of the glass itself. This derivatization is a covalent process and results in the permanent alteration of the glass fiber surface. The silyl TMA and silyl CSP are bifunctional reagents. The reagents are attached to the glass through the silyl groups allowing the other functional group free to interact with the protein or peptide. Since the reagent is covalently attached and since it is in a monolayer on the surface of the glass, it cannot form a matrix which envelopes the sample. The sample must interact with the free functional groups through a combination of electrostatic and hydrophobic forces. This type of interaction is very desirable because it allows the sample to interact with reactants directly, unencumbered by a matrix through which chemicals must diffuse.

While it is possible to make one type of derivatized glass support which will work for both short peptides and proteins, we have found it advantageous to customize the surface for either small or large molecules. Glass derivatized with only silyl-CSP works very well as an anchor for small molecules (peptides with molecular weights under 8000 daltons). Larger peptides and proteins also adhere well to this surface but PTH amino acids with positively charged side chains are not efficiently extracted from the support and give very low yields upon subsequent analysis. If the glass surface is treated first with silyl-CSP and then silyl-TMA, this effect is greatly reduced without affecting the ability of the surface to retain the sample. "Problem" peptides may be sequenced by adjusting the ratios of the two silanes attached to the glass surface (FIG. 2). Pure silyl-TMA derivatized glass works well as a support for large molecules (peptides and proteins with molecular weights over 8000 daltons), but is less satisfactory at retaining smaller peptides on the support surfaces.

Although the specific chemicals mentioned above for silyl derivatized supports are used in the preferred embodiment, modified derivatives containing the same or similar functional groups may work as well or better. For example, any appropriate acid group with a sufficiently low pKa ($<1$) may be substituted for the sulfonic acid group in the preferred embodiment. Examples of other acids which fall into this category include but are not limited to phosphoric, picric, hydrochloric, trifluoroacetic, trichloracetic, chromic, hydroiodic, pyrophosphoric, among others. We have found that the presence of the acidic group is critical to the performance of the peptide support. Omitting the acid group and using a compound such as phenethyltrimethoxy silane results in a support which does not retain peptides, independent of the percentage of chemical used in the derivatization. If a compound such as 3-(trimethylsilyl)-1-propane sulfonic acid is used, a compound which lacks a phenyl ring but has an acid group, the resulting derivatized surface retains peptides. Evidently, it is the presence of the acid group and not the phenyl ring or carbon chain which promotes sample retention. However, since this compound is a solid at room temperature, it is much less convenient to use than the silyl-CSP.

Similarly, the silyl-TMA may be replaced by another quaternary ammonium group bearing compound which covalently binds to glass.

BRIEF DESCRIPTION OF THE DRAWINGS

FIG. 1 compares the yield of PTH-proline in the first cycle of analysis of a decapeptide using a gas-phase sequencer with (a) a support treated with polybrene or (b) a silyl-CSP/TMA derivatized support.

DETAILED DESCRIPTION OF THE INVENTION

Figure 2B:
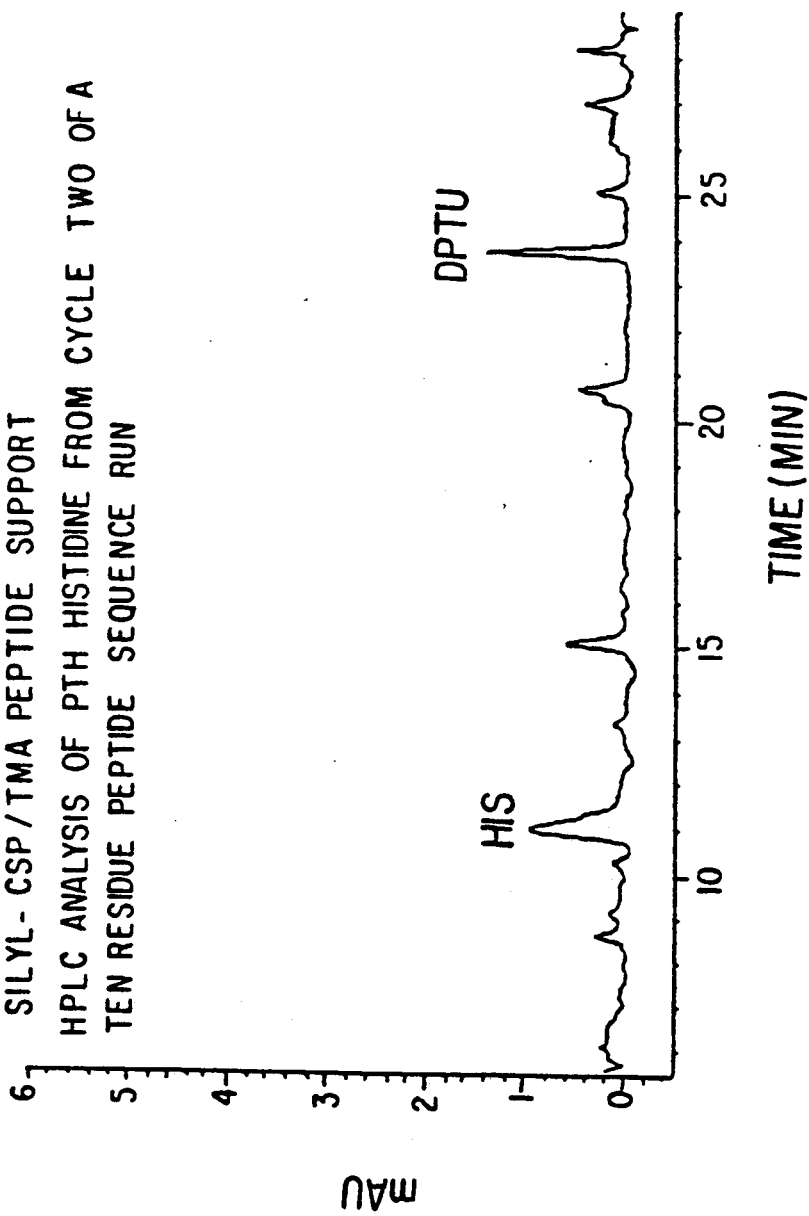
FIG. 2 compares the yield of PTH-histidine in cycle 2 of the analysis of the same decapeptide, using a gas-phase sequencer with (a) a polybrene-treated support, (b) a silyl-CSP/TMA derivatized support, and (c) a silyl-CSP/TMA derivatized support with reduced CSP relative to support (b).

The present invention is thus directed, in one embodiment, to the use of a silica-binding substance having a poly (amino) acid-reactive group to prepare a support suitable for sequencing peptides and/or proteins. The silica-binding substance is preferably an organosilane, having the formula $R_nSiX_{(4-n)}$, where n is 1 to 3 and X is the group which reacts with the inorganic substance. X is a hydrolyzable group, typically, akloxy, acyloxy, amine or chlorine. The most common alkoxy groups are methoxy and ethoxy. R is a nonhydrolyzable organic radical that possesses a functionality that interacts with amino acids.

The preferred concentration is 0.25-2% (v/v) of silica-binding substance in the solvent after dilution.

The support is preferably derivatized with an anionic silane such as the hydrolyzed form of silyl-CSP, or with both an anionic silane and a cationic silane such as silyl-TMA.

The chlorosulphonyl group on the silyl-CSP compound is known to react with primary and secondary amines. Thus, using this active group in the presence of peptides or proteins will block them to sequence analysis by the Edman degradation, which requires a free amino group for the coupling reaction. To overcome this problem, the chlorosuphonyl group is quantitatively converted to the sulfonic acid derivative. This hydrolysis reaction conveniently occurs during the procedure for attaching the silyl-CSP to the glass surface.

The glass surface then has negatively charged sulfonic acid groups with a very low pKa ($<1$). This greatly facilitates the binding of positively charged molecules to the glass. However, we have observed that peptides with a net negative charge and those which are neutral in charge also bind well and are not removed from the surface during the sequencing procedure. From experiments conducted with other types of derivatized glass supports, it appears that the peptide is most likely to be removed from the surface during the ATZ solvent extraction following the acid cleavage step of the Edman degradation. At this point, the peptide will have a net positive charge, no matter what its composition may be, due to the fully protonated N-terminal amino group. If the pKa of the surface groups is sufficiently low, the surface will still have a net negative charge promoting electrostatic interaction with the peptide. The ATZ amino acid derivative is a small uncharged hydrophobic molecule under these conditions and will be easily extracted with solvent away from the charged peptide. The only exceptions will be ATZ histidine and ATZ arginine which will have a net positive charge and thus be more difficult to extract. In fact, if the surface of the glass has too high a concentration of sulfonic acid groups, ATZ His and Arg will be quantitatively retained on the support during extraction.

Lysine, which may be positively charged under acidic conditions, will not be charged after the first Edman coupling reaction since the epsilon-amino group reacts with PITC to form the epsilon-PTC derivative making ATZ lysine very hydrophilic and easily extracted.

During the coupling reaction, a basic environment maintains a net negative charge on the support. The peptide will also be negatively charged via the carbonyl group since the amino terminus is involved in the neutral PTC group. During extraction of coupling reaction by-products the peptide remains on the support even though the electrostatic environment would appear to be unfavorable.

Evidently, a number of effects are combining to form a very strong attractive force. Perhaps partial positive charges within the derivatized peptide bind it to the highly negative surface. This highly desirable effect is somewhat offset for very short hydrophobic peptides since a lower CSP to TMA ratio (See FIG. 3) may lower their affinity for the support and result in poor yields of PTH amino acids as the sequencing run nears the carboxyl terminus. With more hydrophilic peptides, this is not the case and yields near the C-terminus are still good.

In the pure silyl-CSP support, the preferred concentration of silyl CSP in the solution applied to the glass is 1-2%. In the hybrid silyl-CSP/silyl TMA support, the preferred concentration of silyl-CSP is 0.1 to 0.25% and the preferred concentration of silyl-TMA is 0.5-2.0%. A pure silyl-TMA support may also be prepared.

We have found that the method used for the preparation of the glass surface is very critical to the performance of the supports in protein sequencers. Previously published methods for silyl derivatization of glass for use in protein sequences have proven to be very unreliable. Many of these methods require extensive pretreatment of the surface to be derivatized with various acids (so-called "acid etching") and bases to make the silylization successful. We have found these pretreatment methods completely unnecessary and in most cases detrimental. In particular, rinsing with solvent prior to heat treatment is undesirable. The following methods produce surfaces with consistently high affinity for proteins and peptides. These examples illustrate the preparation and use of the preferred embodiments of the present invention.

Example 1

The following example illustrates a method which yields a surface with a very high affinity for poly(amino) acid molecules over about 8000 daltons. It allows sequence analysis on very low quantities of sample. Indeed, the detection method used in the PTH analysis is the limiting factor rather than the amount of sample sequenced. A silyl-TMA derivatized glass surface for use as a protein support is prepared as follows:
1. Pour 95 ml of HPLC-grade methanol into a 100 ml glass graduated cylinder and add 5 ml HPLC-grade water.
2. Mix well and add 6 ml of a 50% solution of silyl TMA in methanol. (The effective concentration is thus about 3% of silyl-TMA).
3. Mix well and let stand for 5 mins., to allow hydrolysis of the silyl groups to take place—do not let stand for more than 5 minutes.
4. Pour the solution into glass petri dishes.
5. Place glass fiber disks (e.g., Whatman GF/F or GF/C glass fiber disks) into the solution, being certain to wet them completely.
6. Incubate for 5 minutes with frequent shaking and turning as necessary to ensure good exposure of the glass to the solution—it is important to keep the disks completely covered with solution.
7. At the end of 5 minutes hang the disks in an oven at 110° C. for 30 minutes. Do not rinse the disks with solvent prior to heat treatment.
8. While the disks are in the oven, discard the solution in the petri dishes and replace it with fresh methanol.
9. At the end of the oven incubation, remove the disks and place them in the dishes containing methanol and rinse thoroughly by swirling.
10. Place each disk into a Buchner filter funnel and wash with three funnel volumes of methanol using gravity feed.
11. Place the washed disks into the vacuum chamber and dry at room temperature for at least 30 minutes.

Other glass supports may be used in place of Whatman GF/F or GF/C filters.

The pure silyl-TMA support does not readily retain peptides of less than 30-40 amino acids. The pure silyl-CSP support or the hybrid support are preferred for sequencing short peptides.

EXAMPLE 2

A silyl-CSP derivatized glass support is preferred for use as a peptide support if histidine and arginine are not in the peptide. This type of surface strongly retains ATZ histidine and ATZ arginine so that they are not extracted well from the reaction support. Adding a compound such as silyl-TMA as outlined in example 3 below greatly reduces this effect, possibly by competing for the negative sites present on the silyl-CSP surface. A pure silyl-CSP surface for use as a peptide support is prepared as in Example I, but adding 2 ml of a 50% solution of silyl-CSP in methylene chloride. (After step 2, the effective concentration is 1% of silyl-CSP).

Example 3

A mixed silyl-CSP/silyl-TMA derivatized glass surface for use as a peptide or protein support may also be made, and this is the most preferred support. The mixture offers superior peptide performance as compared to pure silyl-CSP or pure silyl-TMA since PTH histidine and PTH arginine are extracted well yet surface affinity for even small hydrophobic peptides is excellent. Pure silyl-TMA does not work at all on most small peptides. The mixed support is prepared by first preparing a silyl-CSP support as in Example 2, but with 0.5 ml of a 50% solution of silyl-CSP in methylene chloride (i.e., 0.25% after dilution), and then following the Method of Example 1, but with 4 ml of a 50% silyl-TMA in methanol (i.e., 2% after dilution).

Example 4

FIG. 1 illustrates the value of the hybrid CSP/TMA support for peptide analysis. The decapeptide Pro-His-Pro-Phe-His-Phe-Phe-Val-Tyr-Lys (200 PM) was loaded onto an automated gas-phase sequencer (Porton Instruments PI 2020). This decapeptide presents a considerable challenge to most automated gas or gas/liquid-phase sequencers because of its extremely hydrophobic C-terminal.

The sequencer was equipped with either the hybrid CSP/TMA support of Example 3, or a support treated with Polybrene. The latter support was prepared by pipetting 1.5 mg polybrene in 15 ul H$_2$O onto an underivatized glass fiber support, and permitting it to evaporate. As is seen in FIG. 1, the support treated with Polybrene (1A) gives a much higher background level of artifacts (peaks marked "*") than does the CSP/TMA support during the first analytical cycle.

Example 5

FIG. 2 shows the result of modifying the CSP/TMA ratio from .0.25% CSP/2% TMA (FIG. 2B) to 0.1% CSP/2% TMA (FIG. 2C). The selection of the latter ratio greatly increased the yield of PTH-histidine in cycle 2. The silyl CSP component of the hybrid support usually should not exceed a concentration of 1%, and 0.25% is preferred. When sequencing a peptide known to be rich in His or Arg, use of a hybrid support prepared using an even lower silyl-CSP concentration may be desirable.

Example 6

Figure 3:
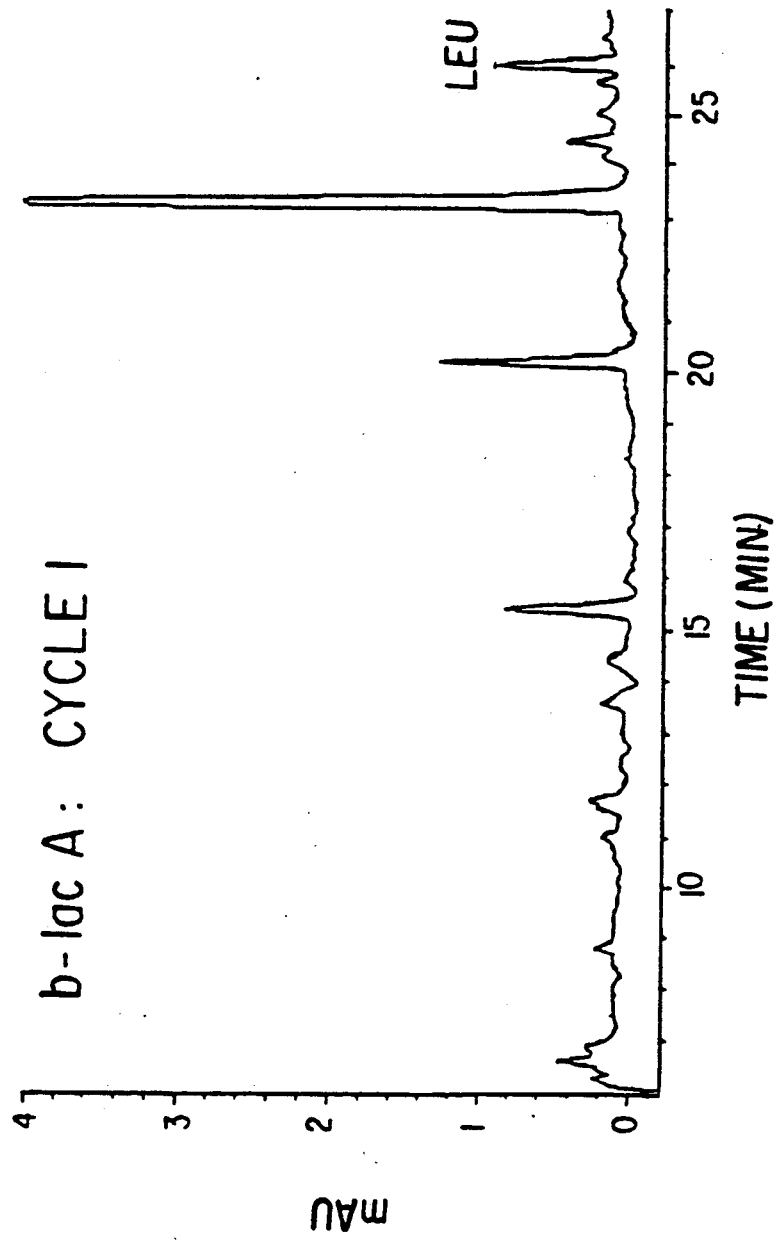
FIG. 3 shows the first 15 cycles of a gas-phase sequencer run of 8 picamoles of beta-lactoglobulin A using the silyl-TMA support.
Figure 3A:
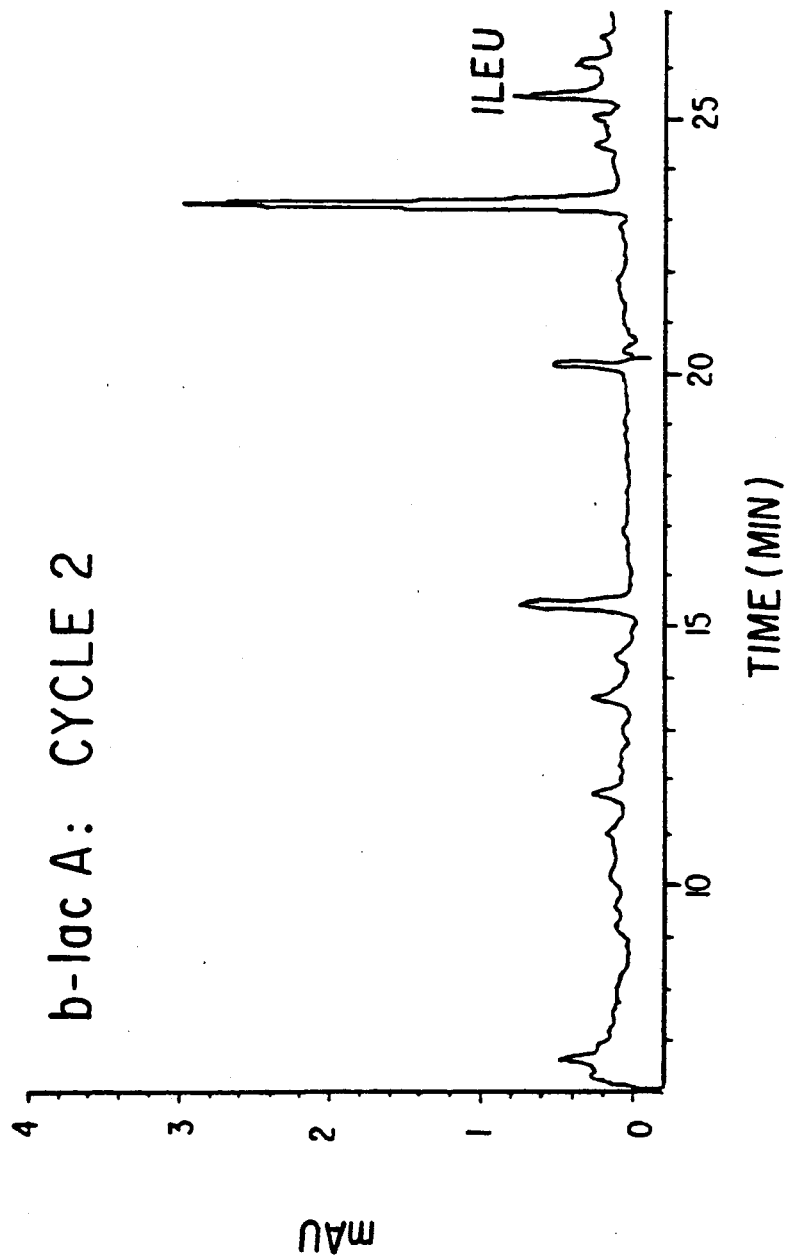
Figure 3B:
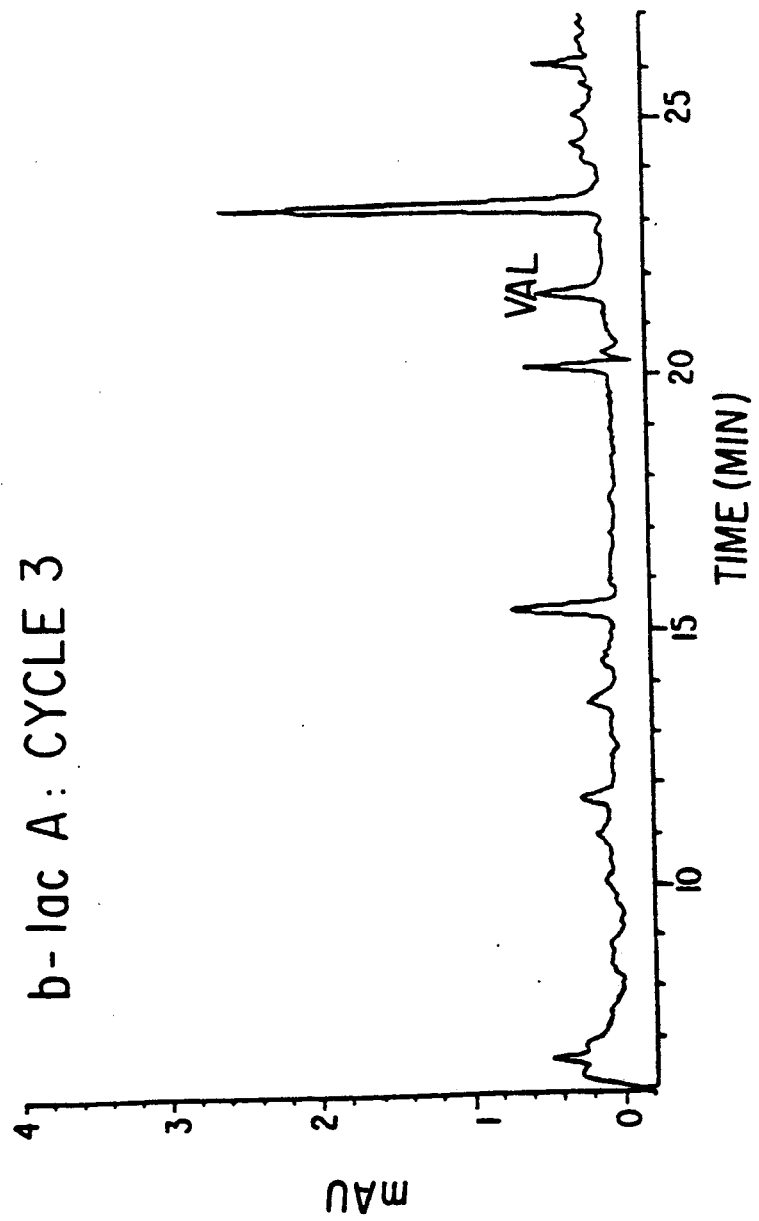
Figure 3D:
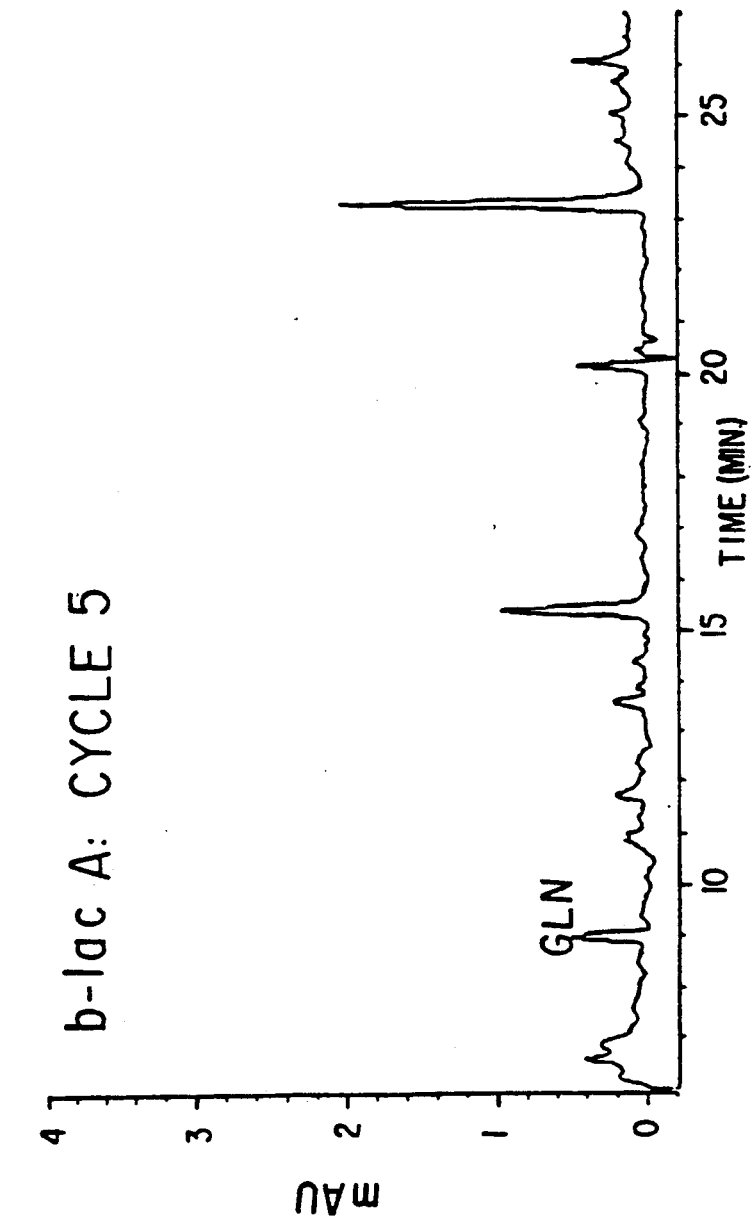
Figure 3E:
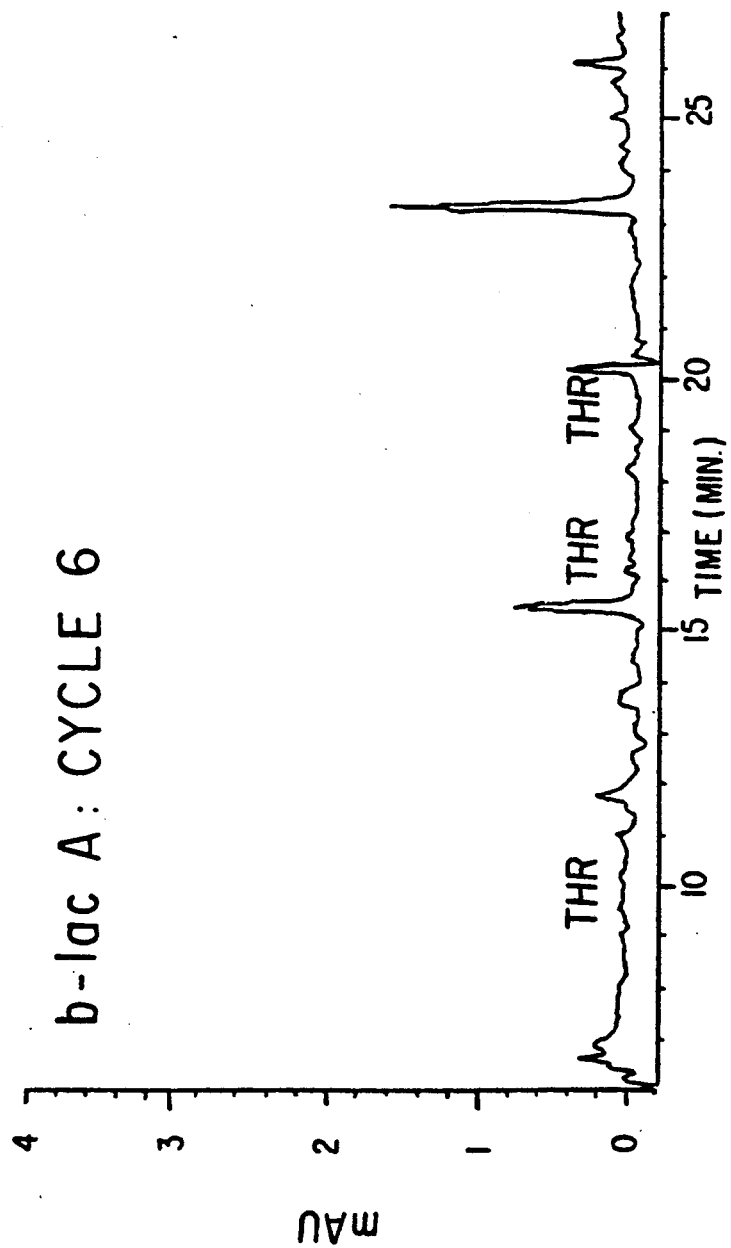
Figure 3I:
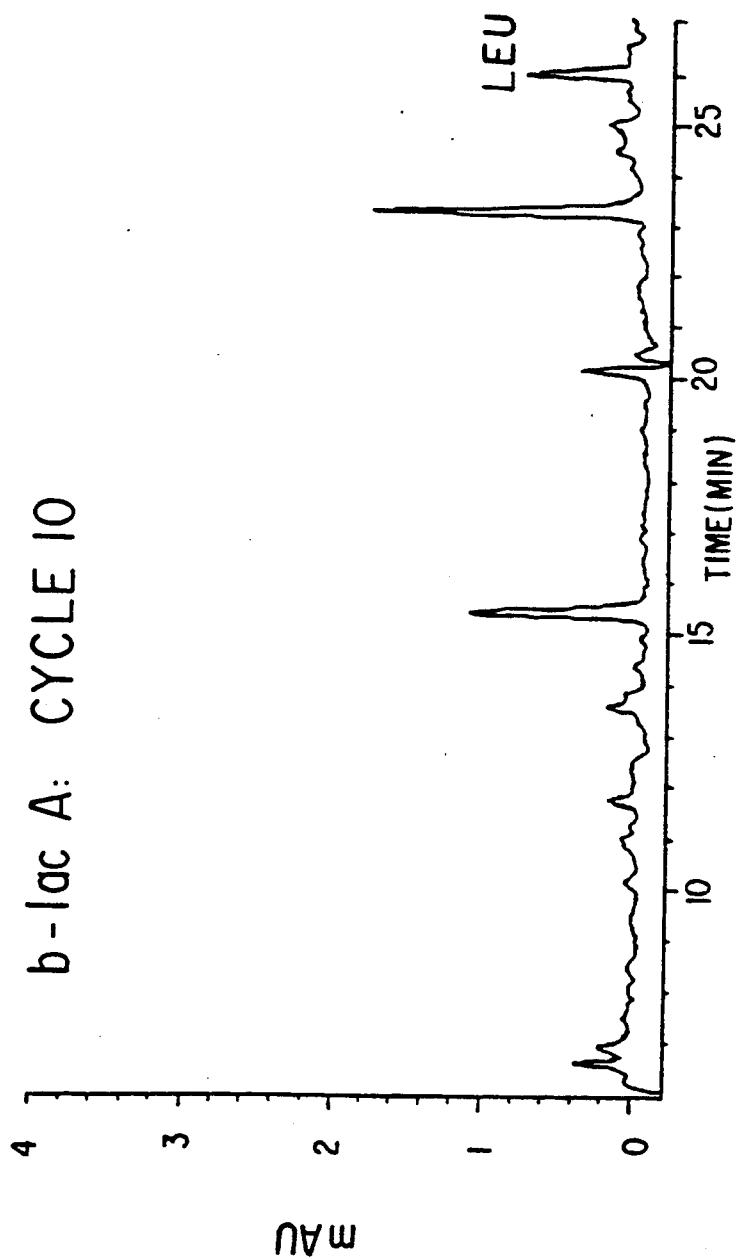
Figure 3J:
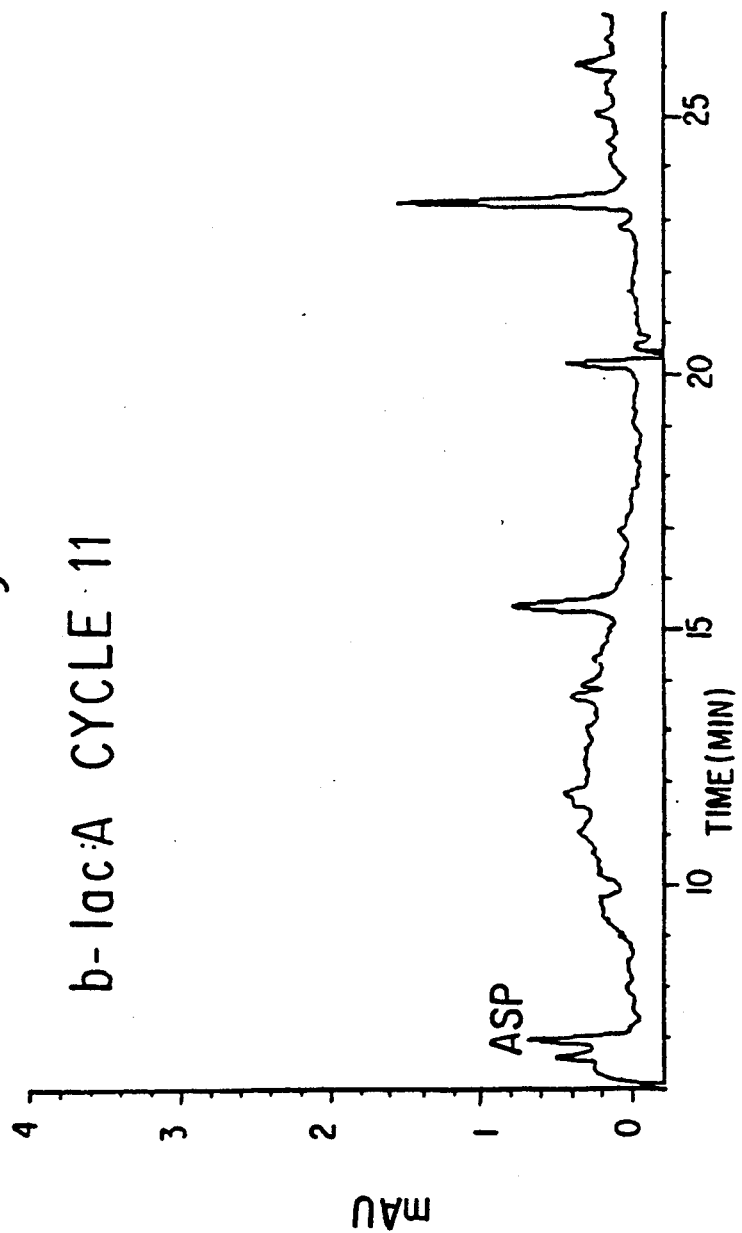

FIG. 3 shows the first 15 cycles of gas-phase sequencer run of beta-lactoglobulin A and illustrates the excellent performance of the silyl-TMA protein support with quantities of sample which approach the detecting limit of the analytical system. Only 8 picomoles of protein were loaded onto the support yet the sequence can be easily determined by visual observation. In this experiment, 75% of the PTH amino acid delivered to the sequencer's fraction collector was analyzed. The yield of PTH leucine at cycle one is greater than 60% and the repetitive yield between PTH valine at cycle 3 and cycle 15 is greater than 95%.

Example 7

Treatment of a pure 2% silyl-CSP support with 150 ug of polybrene greatly reduced the retention of the peptide and thus the yield of the PTH derivatives of the analyzed decapeptide. But if 1.5 mg of polybrene is added, the retention of peptide is comparable to that of Polybrene treated underivatized glass supports.

If the silyl-CSP support worked by embedding the sample, then adding a small amount of additional embedding agent (i.e., Polybrene) should not result in a loss of sample retention. If, however, the Porton support works on a principle based on electrostatic interaction with the sample, adding a small amount of a polybase (i.e., positively charged) substance such as Polybrene would very likely interfere with the electrostatic attraction of the negatively charged support for the sample. This small amount of polybase is not sufficient, however, to embed the sample. Adding more Polybrene (>1.5 mg) will completely cover the charged groups on the support and embed the sample.

I claim:

1. A derivatized glass support comprising a silicaceous support derivatized with a first silica-binding substance having a free acid group, said acid group having a pKa<1, and a second silica-binding substance having a free quaternary ammonium group, said support being capable of retaining a peptide or protein.

2. The support of claim 1 wherein said acid group is selected from the group consisting of phosphoric, picric, hydrochloric, trifluoroacetic, trichloracetic, chromic, hydroiodic, pyrophosphoric, sulfonic and halosulfonic acids.

3. The support of claim 1 in which the acid group is a sulfonic or halosulfonic acid.

4. The support of claim 3 in which the support was prepared by incubating a glass support with a 4-chlorosulfonyl phenyl alkyl alkoxysilane.

5. The support of claim 4 in which the silane was 2-(4-chlorosulfonyl phenyl) ethyl trimethyoxysilane.

6. The support of claim 4 in which the silane was 3-(trimethylsilyl)-1-propane sulfonic acid.

7. The support of claim 1 in which the first substance is 2-(4-chlorosulfonyl phenl) ethyl trimethoxysilane, and the second substance is N-trimethoxysilyl propyl -N, N, N-trimethyl ammonium chloride.

8. The support of claim 1 in which the first or second substance was an organosilane.

9. The support of claim 8 in which the second substance was N-trimethoxysilyl propyl-N,N,N-trimethyl ammonium chloride.

* * * * *